United States Patent
Briscoe (10) Patent No.: US 7,871,409 B2
(45) Date of Patent: *Jan. 18, 2011

(54) ENDOCARDIAL DISPERSIVE ELECTRODE FOR USE WITH A MONOPOLAR RF ABLATION PEN

(75) Inventor: Roderick E. Briscoe, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/364,232

(22) Filed: Feb. 2, 2009

(65) Prior Publication Data
US 2009/0138008 A1 May 28, 2009

Related U.S. Application Data

(62) Division of application No. 10/425,531, filed on Apr. 29, 2003, now Pat. No. 7,497,857.

(51) Int. Cl.
*A61B 18/14* (2006.01)
*A61B 18/16* (2006.01)

(52) U.S. Cl. .......................................... 606/32; 606/41
(58) Field of Classification Search ................... 606/32, 606/41
See application file for complete search history.

(56) References Cited

U.S. PATENT DOCUMENTS

| | | |
|---|---|---|
| 2,371,978 A | 3/1945 | Perham |
| 3,496,932 A | 2/1970 | Prisk et al. |
| 3,736,936 A | 6/1973 | Basiulis et al. |
| 3,807,403 A | 4/1974 | Stumpf et al. |

(Continued)

FOREIGN PATENT DOCUMENTS

WO 99/62409 12/1999

(Continued)

OTHER PUBLICATIONS

Chitwood. "Will C. Sealy, MD: The Father of Arthythria Surgery—The Story of the Fisherman with a Fast Pulse," Annals of Thoracic Surgery 58:1228-1239, 1994.

(Continued)

*Primary Examiner*—Lee S Cohen
(74) *Attorney, Agent, or Firm*—Mike Jaro; Jeffrey J. Hohenshell (57) ABSTRACT

Methods and devices for forming a lesion in a target tissue having a cavity within. A first RF electrode and a second RF electrode can be coupled to opposite poles of an RF current source. The second electrode can be inserted into the tissue cavity and expanded to contact the target tissue from within. The first electrode can be externally disposed against the target tissue while applying RF current between the first and second electrodes to ablate the target tissue. Some methods are directed to ablating tribiculated atrial wall tissue to treat atrial fibrillation. The second electrode can contact the tribiculated tissue directly from within to provide a direct path between the two electrodes. In some methods, the second electrode is inserted through an incision made to remove an atrial appendage. The methods can provide deeper, narrower lesions relative to those made using remote, indifferent electrodes. Atrial fibrillation ablation procedures can be performed using the invention, requiring fewer incisions than conventional methods.

6 Claims, 3 Drawing Sheets

U.S. PATENT DOCUMENTS

| | | |
|---|---|---|
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,854,482 A | 12/1974 | Laughtery et al. |
| 3,856,016 A | 12/1974 | Davis |
| 3,856,018 A | 12/1974 | Perisse et al. |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,226,239 A | 10/1980 | Polk et al. |
| 4,248,224 A | 2/1981 | Jones |
| 4,274,415 A | 6/1981 | Kanamoto et al. |
| 4,275,734 A | 6/1981 | Mitchiner |
| 4,278,090 A | 7/1981 | van Gerven |
| 4,377,168 A | 3/1983 | Rzasa et al. |
| 4,493,319 A | 1/1985 | Polk et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,791,707 A | 12/1988 | Tucker |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,917,677 A | 4/1990 | McCarthy |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,119,804 A | 6/1992 | Anstadt |
| 5,147,355 A | 9/1992 | Friedman et al. |
| 5,178,133 A | 1/1993 | Pena |
| 5,207,674 A | 5/1993 | Hamilton |
| 5,217,473 A | 6/1993 | Yoon |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,282,829 A | 2/1994 | Hermes |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,334,209 A | 8/1994 | Yoon |
| 5,336,252 A | 8/1994 | Cohen |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,366,459 A | 11/1994 | Yoon |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,425,740 A | 6/1995 | Hutchinson, Jr. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Sliwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,772 A | 11/1996 | Lennox |
| 5,575,788 A | 11/1996 | Baker et al. |
| 5,575,810 A | 11/1996 | Swanson et al. |

| | | | | | |
|---|---|---|---|---|---|
| 5,578,007 A | 11/1996 | Imran | 5,897,553 A | 4/1999 | Mulier et al. |
| 5,582,609 A | 12/1996 | Swanson et al. | 5,897,554 A | 4/1999 | Chia et al. |
| 5,588,432 A | 12/1996 | Crowley | 5,899,898 A | 5/1999 | Arless et al. |
| 5,590,657 A | 1/1997 | Cain et al. | 5,899,899 A | 5/1999 | Arless et al. |
| 5,595,183 A | 1/1997 | Swanson et al. | 5,902,289 A | 5/1999 | Swartz et al. |
| 5,607,462 A | 3/1997 | Imran | 5,904,711 A | 5/1999 | Flom et al. |
| 5,617,854 A | 4/1997 | Munsif | 5,906,580 A | 5/1999 | Kline-Schoder et al. |
| 5,620,452 A | 4/1997 | Yoon | 5,906,587 A | 5/1999 | Zimmon |
| 5,630,837 A | 5/1997 | Crowley | 5,906,606 A | 5/1999 | Chee et al. |
| 5,637,090 A | 6/1997 | McGee et al. | 5,908,029 A | 6/1999 | Knudson et al. |
| 5,643,197 A | 7/1997 | Brucker et al. | 5,916,213 A | 6/1999 | Haissaguerre et al. |
| 5,656,029 A | 8/1997 | Imran et al. | 5,916,214 A | 6/1999 | Cosio et al. |
| 5,658,278 A | 8/1997 | Imran et al. | 5,921,924 A | 7/1999 | Avitall |
| 5,667,518 A | 9/1997 | Pannell | 5,921,982 A | 7/1999 | Lesh et al. |
| 5,671,747 A | 9/1997 | Connor | 5,925,038 A | 7/1999 | Panescu et al. |
| 5,673,695 A | 10/1997 | McGee et al. | 5,927,284 A | 7/1999 | Borst et al. |
| 5,676,662 A | 10/1997 | Fleischbacker et al. | 5,928,191 A | 7/1999 | Houser et al. |
| 5,676,692 A | 10/1997 | Sanghvi et al. | 5,931,810 A | 8/1999 | Grabek |
| 5,676,693 A | 10/1997 | Lafontaine | 5,931,848 A | 8/1999 | Saadat |
| 5,678,550 A | 10/1997 | Bassen et al. | 5,938,694 A | 8/1999 | Jaraczewski et al. |
| 5,680,860 A | 10/1997 | Imran | 5,954,661 A | 9/1999 | Greenspon et al. |
| 5,681,278 A | 10/1997 | Igo et al. | 5,971,980 A | 10/1999 | Sherman |
| 5,681,308 A | 10/1997 | Edwards et al. | 5,971,983 A | 10/1999 | Lesh |
| 5,687,723 A | 11/1997 | Avitall | 5,984,917 A | 11/1999 | Fleischman et al. |
| 5,687,737 A | 11/1997 | Branham et al. | 5,989,284 A | 11/1999 | Laufer |
| 5,688,267 A | 11/1997 | Panescu et al. | 5,993,447 A | 11/1999 | Blewett et al. |
| 5,690,611 A | 11/1997 | Swartz et al. | 6,007,499 A | 12/1999 | Martin et al. |
| 5,697,536 A | 12/1997 | Eggers et al. | 6,012,457 A | 1/2000 | Lesh |
| 5,697,882 A | 12/1997 | Eggers et al. | 6,016,811 A | 1/2000 | Knopp et al. |
| 5,697,925 A | 12/1997 | Taylor | 6,042,556 A | 3/2000 | Beach et al. |
| 5,697,927 A | 12/1997 | Imran et al. | 6,042,563 A | 3/2000 | Morejohn et al. |
| 5,697,928 A | 12/1997 | Walcott et al. | 6,063,081 A | 5/2000 | Mulier et al. |
| 5,713,942 A | 2/1998 | Stern | 6,071,279 A | 6/2000 | Whayne et al. |
| 5,716,389 A | 2/1998 | Walinsky et al. | 6,088,894 A | 7/2000 | Oakley |
| 5,718,241 A | 2/1998 | Ben-Haim et al. | 6,096,037 A | 8/2000 | Mulier et al. |
| 5,718,701 A | 2/1998 | Shai et al. | 6,113,592 A | 9/2000 | Taylor |
| 5,720,775 A | 2/1998 | Larnard | 6,117,101 A | 9/2000 | Diederich et al. |
| 5,722,402 A | 3/1998 | Swanson et al. | 6,120,496 A | 9/2000 | Whayne et al. |
| 5,730,074 A | 3/1998 | Peter | 6,142,993 A | 11/2000 | Whayne et al. |
| 5,730,127 A | 3/1998 | Avitall | 6,142,994 A | 11/2000 | Swanson et al. |
| 5,730,704 A | 3/1998 | Avitall | 6,152,144 A | 11/2000 | Lesh et al. |
| 5,733,280 A | 3/1998 | Avitall | 6,152,920 A | 11/2000 | Thompson et al. |
| 5,735,280 A | 4/1998 | Sherman et al. | 6,161,543 A | 12/2000 | Cox et al. |
| 5,735,290 A | 4/1998 | Sterman et al. | 6,165,174 A | 12/2000 | Jacobs et al. |
| 5,755,760 A | 5/1998 | Maguire et al. | 6,217,528 B1 | 4/2001 | Koblish et al. |
| 5,769,846 A | 6/1998 | Edwards et al. | 6,217,576 B1 | 4/2001 | Tu et al. |
| 5,779,699 A | 7/1998 | Lipson | 6,224,592 B1 | 5/2001 | Eggers et al. |
| 5,782,828 A | 7/1998 | Chen et al. | 6,231,518 B1 | 5/2001 | Grabek et al. |
| 5,785,706 A | 7/1998 | Bednarek | 6,231,561 B1 | 5/2001 | Frazier et al. |
| 5,788,636 A | 8/1998 | Curley | 6,235,024 B1 | 5/2001 | Tu |
| 5,792,140 A | 8/1998 | Tu et al. | 6,237,605 B1 | 5/2001 | Vaska et al. |
| 5,797,960 A | 8/1998 | Stevens et al. | 6,238,347 B1 | 5/2001 | Nix et al. |
| 5,800,428 A | 9/1998 | Nelson et al. | 6,238,393 B1 | 5/2001 | Mulier |
| 5,800,482 A | 9/1998 | Pomeranz et al. | 6,241,754 B1 | 6/2001 | Swanson et al. |
| 5,810,802 A | 9/1998 | Panescu et al. | 6,245,061 B1 | 6/2001 | Panescu et al. |
| 5,827,216 A | 10/1998 | Igo et al. | 6,245,064 B1 | 6/2001 | Lesh et al. |
| 5,836,947 A | 11/1998 | Fleischman et al. | 6,245,065 B1 | 6/2001 | Panescu et al. |
| 5,840,030 A | 11/1998 | Ferek-Petric et al. | 6,251,092 B1 | 6/2001 | Qin et al. |
| 5,844,349 A | 12/1998 | Oakley et al. | 6,251,128 B1 | 6/2001 | Knopp et al. |
| 5,846,187 A | 12/1998 | Wells et al. | 6,254,598 B1 | 7/2001 | Edwards et al. |
| 5,846,191 A | 12/1998 | Wells et al. | 6,270,471 B1 | 8/2001 | Hechel et al. |
| 5,849,028 A | 12/1998 | Chen | 6,280,415 B1 | 8/2001 | Johnson |
| 5,871,523 A | 2/1999 | Fleischman et al. | 6,290,674 B1 | 9/2001 | Roue et al. |
| 5,871,525 A | 2/1999 | Edwards et al. | 6,293,943 B1 | 9/2001 | Panescu et al. |
| 5,873,845 A | 2/1999 | Cline et al. | 6,296,619 B1 | 10/2001 | Brisken et al. |
| 5,876,399 A | 3/1999 | Chia et al. | 6,302,880 B1 | 10/2001 | Schaer |
| 5,879,295 A | 3/1999 | Li et al. | 6,311,692 B1 | 11/2001 | Vaska et al. |
| 5,879,296 A | 3/1999 | Ockuly et al. | 6,312,383 B1 | 11/2001 | Lizzi et al. |
| 5,881,732 A | 3/1999 | Sung et al. | 6,314,962 B1 | 11/2001 | Vaska et al. |
| 5,882,346 A | 3/1999 | Pomeranz et al. | 6,314,963 B1 | 11/2001 | Vaska et al. |
| 5,885,278 A | 3/1999 | Fleischman | 6,325,797 B1 | 12/2001 | Stewart et al. |
| 5,893,848 A | 4/1999 | Negus et al. | 6,328,736 B1 | 12/2001 | Mulier |
| 5,895,417 A | 4/1999 | Pomeranz et al. | 6,332,881 B1 | 12/2001 | Carner et al. |

| | | |
|---|---|---|
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,554 B1 | 7/2002 | Alferness et al. |
| 6,419,648 B1 | 7/2002 | Vitek et al. |
| 6,425,867 B1 | 7/2002 | Vaezy et al. |
| 6,428,548 B1 | 8/2002 | Durgin et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,485,407 B2 | 11/2002 | Alferness et al. |
| 6,488,680 B1 | 12/2002 | Francischelli |
| 6,491,706 B1 | 12/2002 | Alferness et al. |
| 6,502,575 B1 | 1/2003 | Jacobs et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 5,697,536 C1 | 6/2003 | Eggers et al. |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,793,664 B2 | 9/2004 | Mazzocchi et al. |
| 6,807,968 B2 | 10/2004 | Francischelli |
| 6,827,715 B2 | 12/2004 | Francischelli |
| 6,849,073 B2 | 2/2005 | Hoey |
| 6,849,075 B2 | 2/2005 | Bertolero et al. |
| 6,849,078 B2 | 2/2005 | Durgin et al. |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,115,122 B1 | 10/2006 | Swanson et al. |
| 7,497,857 B2 * | 3/2009 | Briscoe ................. 606/32 |
| 2001/0039434 A1 | 11/2001 | Frazier et al. |
| 2001/0039435 A1 | 11/2001 | Roue et al. |
| 2002/0022833 A1 | 2/2002 | Maguire |
| 2002/0022860 A1 | 2/2002 | Borillo et al. |
| 2002/0035374 A1 | 3/2002 | Borillo et al. |
| 2002/0049457 A1 | 4/2002 | Kaplan et al. |
| 2002/0099390 A1 | 7/2002 | Kaplan et al. |
| 2002/0103492 A1 | 8/2002 | Kaplan et al. |
| 2002/0111641 A1 | 8/2002 | Peterson et al. |
| 2002/0169377 A1 | 11/2002 | Khairkhahan et al. |
| 2002/0177859 A1 | 11/2002 | Monassevitch et al. |
| 2003/0018362 A1 | 1/2003 | Fellows et al. |
| 2003/0023266 A1 | 1/2003 | Borillo et al. |
| 2003/0045872 A1 | 3/2003 | Jacobs |
| 2003/0055422 A1 | 3/2003 | Lesh |
| 2003/0060821 A1 | 3/2003 | Hall et al. |
| 2003/0065319 A1 | 4/2003 | Wellman |
| 2003/0144656 A1 | 7/2003 | Ocel |
| 2003/0158464 A1 | 8/2003 | Bertolero |
| 2003/0191462 A1 | 10/2003 | Jacobs |
| 2003/0195496 A1 | 10/2003 | Maguire |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0073241 A1 | 4/2004 | Barry et al. |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0149068 A1 | 7/2005 | Williams et al. |
| 2005/0149069 A1 | 7/2005 | Bertolero et al. |
| 2005/0165392 A1 | 7/2005 | Francischelli |
| 2005/0209564 A1 | 9/2005 | Bonner |
| 2005/0267454 A1 | 12/2005 | Hissong |
| 2005/0277959 A1 | 12/2005 | Cosgrove et al. |
| 2006/0009756 A1 | 1/2006 | Francischelli |
| 2006/0009759 A1 | 1/2006 | Christian |
| 2006/0020271 A1 | 1/2006 | Stewart et al. |

FOREIGN PATENT DOCUMENTS

| | | |
|---|---|---|
| WO | 01/35832 | 5/2001 |
| WO | 01/87169 | 11/2001 |
| WO | 01/97696 | 12/2001 |
| WO | 02/087456 | 11/2002 |
| WO | 03/011150 | 2/2003 |
| WO | 03/096881 | 11/2003 |
| WO | 2004/096070 | 11/2004 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Gairandon et al., "Surgical Repair of Wolff-Parkinson-White Syndrome: A New Closed-Heart Techique," The Annals of Thoracic Surgery 37(1): 67-71, 1984.

Klien et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5):495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): 1-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results." The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Nardella, "Radio Frequency Energy and Impedance Feedback," SPIE vol. 1068, Catheter Based Sensing and Imaging Technology (1989).

Avitail et. al., "A Thoracoscopic Approach to Ablate Atrial Fibrillation Via Linear Radiofrequency Lesion Generation on the Epicardium of Both Atria," PACE, Apr. 1996; 19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:1450,#2519.

Jais et al., "Catheter Ablation for Paroxysmal Atrial Fibrillation: High Success Rates with Ablation in the Left Atrium," Circulation (Nov. 1996) 94:1-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation." Ann Thorac Surg. 1993; 56:814-824.

Avitall et al., "New Monitoring Critriea for Transmural Ablation of Atrial Tissues," Circulation, 1996;94(Supp 1);1-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrquency Catheter Therapy of Paroxysmal Atrial Fibrilliation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Desease." JACC, 1996;28(4):985-990.

Cox, et al., "Perinodal cryosurgery for atriovenrical node reentry tachycardia in 23 patients," Journal of Thoracic and Cardiovascular Surgery. 99:3, Mar. 1990, pp. 440-450.

Cox, "Anatomic-Electrophysiologic Basis for the Surgical Treatment of Refractory Ischemic Ventrical Tachycardia," Annals of Surgery, Aug. 1983; 198:2:119-129.

Williams, et al., "Left atrial isolation," J Thorac Cardiovasc Surg:1980; 80:373-380.

Schienman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg. 1997;63:1070-1075.

Cox, JL, "The Surgical Treatment of Atrial Fibrillation IV. Surgical Technique," Thoracic and Cardiovascular Surgery, 101(4):584-592, 1991.

Sueda, et al., "Simple Left Atrial Procedur for Chronic Atrial Fibrillation Associated with Mitral Valve Disease," Ann Thorac Surgery 1996; 62:1976-800.

Nellens, et al., "Transcoronary Chemical Ablation of Arrhythmias?" PACE 15(Suppl:SEp.):1368-1373, 1992.

Weismuller, et al., "Chemical Ablation by Subendocardial Injection of Ethanol via Catheter—Preliminary Results in the Pig Heart," European Heart Journal 12:1234-1327, 1991.

* cited by examiner

ENDOCARDIAL DISPERSIVE ELECTRODE FOR USE WITH A MONOPOLAR RF ABLATION PEN

This application is a divisional application of U.S. patent application Ser. No. 10/425,531 filed Apr. 29, 2003, now U.S. Pat. No. 7,497,857.

FIELD OF THE INVENTION

The present invention relates generally to devices for cardiac surgery, and more specifically to devices for ablation of cardiac tissue.

BACKGROUND OF THE INVENTION

The present invention is directed toward treatment of tachyarrhythmias, which are heart rhythms in which one or more chambers of the heart exhibit an excessively fast rhythm. In particular, the present invention is directed toward treatment of tachycardias, which are due to the presence of ectopic foci within the cardiac tissue or due to the presence of aberrant condition pathways within the cardiac tissue.

There are many medical treatments that involve instances of cutting, ablating, coagulating, destroying, or otherwise changing the physiological properties of tissue. These techniques can be used beneficially to change the electrophysiological properties of tissue. For example, ablation of cardiac tissue can be used to cure various cardiac conditions. Normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node (or "AV node") and the bundle of HIS (or "HIS bundle") to myocardial tissue cells of the ventricles. The depolarization of these cells propagates across the ventricles, causing the ventricles to contract. This conduction system results in the described, organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles.

The aberrant conductive pathways create abnormal, irregular, and sometimes life-threatening heart rhythms, called arrhythmias. An arrhythmia can take place in the atria, for example, as in atrial tachycardia, atrial fibrillation or atrial flutter. The arrhythmia can also take place in the ventricle, for example, as in ventricular tachycardia.

The lesions used to treat atrial fibrillation, are typically long and thin and are carefully placed to interrupt the conduction routes of the most common reentry circuits. More specifically, the long thin lesions are used to create a maze pattern that creates a convoluted path for electrical propagation within the left and right atria. The lesions direct the electrical impulse from the SA node along a specified route through all regions of both atria, causing uniform contraction required for normal atrial transport function. The lesions finally direct the impulse to the AV node to activate the ventricles, restoring normal atrioventricular synchrony. Several surgical approaches have been developed with the intention of treating atrial fibrillation. One particular example is known as the "maze procedure," as is disclosed by Cox, J L et al. in "The surgical treatment of atrial fibrillation. I. Summary" Thoracic and Cardiovascular Surgery 101(3), pp. 402-405 (1991); and also by Cox, J L in "The surgical treatment of atrial fibrillation. IV. Surgical Technique", Thoracic and Cardiovascular Surgery 101(4), pp. 584-592 (1991), both of which are incorporated by reference herein in their entireties. In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996), which is incorporated herein by reference in its entirety.

When modifying the electrophysiological properties of cardiac tissue by ablation, or by other means of destroying tissue to create lesions, physicians must carefully place the lesions. Otherwise, tissue will be unnecessarily destroyed. In addition, the heart is in close proximity to nerves and other nervous tissue and the destruction of this tissue will result in severe harm to the patient. Anatomical methods are used to locate the areas to be ablated or otherwise modified. In other words, the physician locates key structures such as the mitral valve annulus and the pulmonary veins. Lesions are typically formed that block propagations near these structures. Additional lesions are then formed which connect these lesions and complete the so-called "maze pattern." However, the exact lesion pattern, and number of lesions created, can vary from patient to patient.

The surgical "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

Injection of alcohol into heart tissue has also been employed to ablate cardiac tissue. Alcohol may be delivered to blood vessels supplying the tissue to be ablated, as described in "Transcoronary Chemical Ablation of Arrhythmias", by Nellens et al, Pace Vol. 15, pages 1368-1373, September 1992. Alternatively, alcohol can be delivered directly to the tissue to be ablated by means of a needle inserted through a catheter, as described in "Chemical Ablation by Subendocardial Injection of Ethanol via Catheter—Preliminary Results in the Pig Heart", by Weismuller et al, European Heart Journal, Volume 12, pages 1234-1239, 1991.

Although successful at treating AF, the surgical maze procedure is quite complex and is currently performed by only a few skilled cardiac surgeons in conjunction with other open-heart procedures. Tools that could reliably duplicate the Maze incisions by other means (e.g. radio frequency, laser, microwave, ultrasound energy) will reduce the time and invasiveness required for the maze procedure and make it more accessible to more surgeons. Problems faced by these methods, however, include (a) the creation of continuous, linear lesions in the atria for the prevention of atrial fibrillation, (b) minimization of clotting and thromboembolism, (c) the effect of heat loss due to circulating blood, (d) minimization of lesion width and minimization of atrial debulking, (e) conforming to an irregular myocardial thickness, (f) adaptability to a variety of lesion geometries and (g) usefulness from either the endocardial surface of an open heart, or the epicardial surface of a beating heart.

One particular procedure, the monopolar RF ablation of cardiac atrial tissue to treat atrial fibrillation, causes wide, shallow lesions, due to current dispersion through the tissue. In heavily tribiculated tissue, monopolar ablation is only feasible endocardially. An epicardial approach using conventional methods will not efficiently transfer energy into the deep tissue folds, due to that tissue being out of the conductive path between the external epicardial electrode and the remote indifferent electrode. Bipolar hemostats have been used to concentrate the current through a direct tissue path between closely spaced electrodes to provide improved ablation through smooth or heavily tribiculated tissue. However, the bipolar hemostats require significant tissue cutting to provide complete access to necessary lesion sites.

Some tissue cutting is required in a Maze procedure. In particular, the atrial appendages are typically removed. Monopolar RF cardiac ablation requires significant additional tissue cutting in order to position the electrode in the proper positions to perform endocardial ablations.

What would be desirable are methods that would reduce tissue cutting and improve the efficacy of epicardial ablation. What would be advantageous are devices that direct RF current along the desired transmural path, creating narrower and deeper lesions.

SUMMARY OF THE INVENTION

The present invention includes devices and methods for ablation of cardiac tissue in which a hand-held, monopolar RF ablation device is used to ablate cardiac tissue in conjunction with an expandable endocardial electrode inserted into a heart chamber and urged against the chamber wall. The endocardial electrode can be expandable or inflatable and have a conductive surface. The endocardial electrode may be inserted through a small incision made in the heart chamber wall and/or through the opening made by the removal of the atrial appendage. The electrode can then be expanded or inflated, urging the conductive surface against the endocardium.

A monopolar RF ablation device can then be drawn along the desired lesion line on the epicardium. A current path is thus formed between the epicardial RF device and the expanded surface electrode disposed against the endocardium. The direct path between the external monopolar RF electrode and the endocardial surface internal electrode can provide a narrower, deeper lesion relative to the lesion created using a current path between the RF electrode and an external, indifferent electrode. The incision required to insert the expandable or inflatable electrode can be significantly smaller than that required to insert and successfully maneuver the monopolar RF electrode endocardially.

The monopolar electrode tissue-contacting surface can be connected to one pole of a radio frequency generator while the other pole of the generator is connected to a large surface, endocardial electrode. In one embodiment of the invention, the epicardial monopolar electrode is a conventional radio frequency ablation device such as the Cardioblate® pen available Medtronic, Inc.

The present invention includes methods for forming a lesion in a target tissue having a cavity within. The methods can include providing a first RF electrode coupled to a RF current source and a second RF electrode electrically coupled to form a ground path for the first RF electrode, wherein the second RF electrode is electrically conductive and expandable, wherein the second electrode has a first, unexpanded configuration and a second, expanded configuration. The second electrode can be inserted into the tissue cavity and expanded to the second configuration to contact the target tissue from within the cavity. The first electrode can be disposed against the target tissue while applying RF current between the first and second electrodes to ablate the target tissue.

The present invention includes methods for treating atrial fibrillation that do not require making any incisions in the right or left atria other than those to remove the left and/or right atrial appendages. The methods can include making lesion paths of the Maze, Maze 3 or Modified Maze 3 procedures, while performing only the incisions to remove the atrial appendages. The methods can include making lesions along the paths described in the: Cox, J L et al.; Cox, J L; and Sueda et al. publications, previously incorporated by reference in the present application.

In one method, an incision is made to remove the right atrial appendage and the method does not include making any other incisions in the right atrium. One such method does not include making an incision from the right atrial appendage incision toward the inferior vena caval orifice. Another such method does not include making a posterior longitudinal incision starting caudal to the superior caval cannulation site at the dorsal aspect of the right atrium.

In another method, an incision is made to remove the left atrial appendage, and the method does not include making any other incisions in the left atrium. One such method does not include making a standard atriotomy in the inter-atrial groove between the left and right atria.

One device includes a shaft and an electrode including an envelope having an interior and an electrically conductive flexible surface disposed near the shaft distal region. The second electrode surface can have a first configuration having a first interior volume within the conductive surface and a second, expanded configuration having a second interior volume within the conductive surface, with the second volume being greater than the first volume.

In some devices, the electrically conductive surface includes an outer metallic layer disposed over a polymeric layer. Some electrodes include an outer metallic mesh disposed over a polymeric layer. The polymeric layer can be substantially resistant to fluid permeation, such that the polymeric layer is inflatable. The envelope can be formed of an electrically conductive polymer. Some envelopes according to the present invention are porous, and the electrically conductive surface can be the outer surface an electrically conductive porous mesh. Some meshes are metallic meshes.

Some device embodiments have a fluid lumen extending through the shaft, which can be used to inflate the envelope. Other embodiments have envelopes biased to expand when unconstrained. Still other embodiment envelopes include shape memory materials that expand when heated to body temperature.

DETAILED DESCRIPTION OF THE INVENTION

Figure 1:
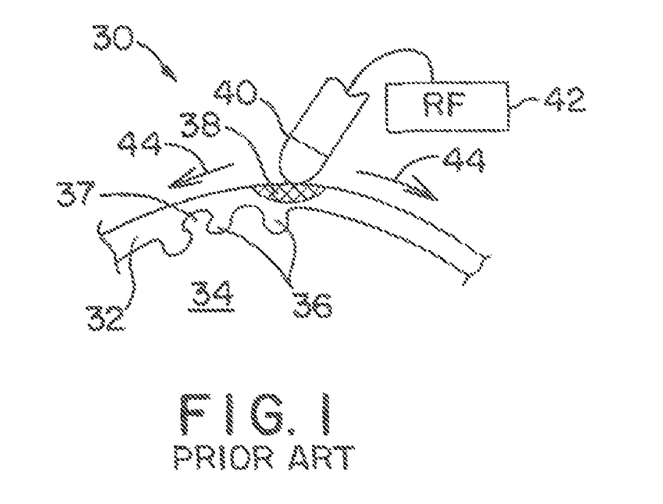
FIG. 1 is a prior art, fragmentary, cross-sectional view of a heart chamber wall having tribiculated tissue, the wall being partially ablated using an external RF electrode and a remote, indifferent electrode.

FIG. 1 illustrates a prior art method for ablating cardiac tissue in the atria. In particular, a tribiculated region of the atria is illustrated. An atrial region 30 is illustrated, having an atrial wall 32, an interior 34, and tribiculated tissue 36 is illustrated, having gaps or cavities 37 disposed between the tribiculated tissue regions. A monopolar electrode 40 is illustrated, coupled to an RF energy source 42. A lesion area 38 formed from the ablation is also illustrated. In FIG. 1, a remote, indifferent electrode (not illustrated in FIG. 1) provides the return path for the RF energy supplied by monopolar electrode 40. As may be seen from inspection of FIG. 1, lesion area 38 is fairly wide, and does not penetrate into tribiculated tissue regions 36. The shallow and insufficiently deep lesions are formed due to the RF current dispersion, indicated at 44, as RF energy takes a path to the indifferent electrode that does not include penetrating directly into atrial wall 32. As maybe seen from inspection of FIG. 1, monopolar ablation of some tissue regions may not be feasible using a monopolar electrode, due to the shallow penetration. In such cases, endocardial ablation, using electrode 40, may be required.

Figure 2:
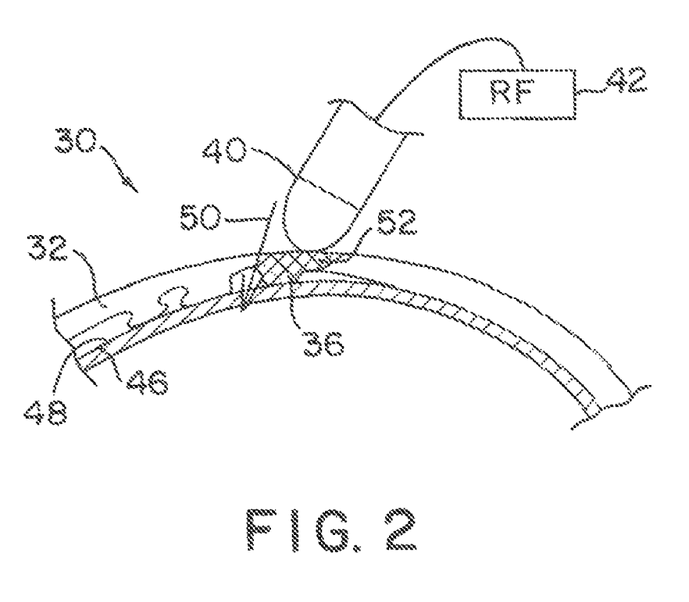
FIG. 2 is a fragmentary, cross-sectional view of the tribiculated heart chamber wall of FIG. 1, being ablated using the RF electrode of FIG. 1 and an internal, expandable surface electrode contacting the tribiculated tissue.

FIG. 2 illustrates atrial region 30 of FIG. 1, using devices and methods according to the present invention. Tribiculated tissue regions 36 may be seen, as discussed with respect to FIG. 1. In FIG. 2 however, a second electrode 46 may be seen, having an envelope surface 48 contacting the tissue of atrial wall 32 and tribiculated tissue regions 36. Second electrode 46 may be described as an envelope or membrane, in various embodiments. Second electrode 46 may be seen to contact tribiculated tissue 36 and other endocardial tissue directly, providing a short, direct current path, indicated at 50, between second electrode 46 and a monopolar electrode 40. As a result of the more direct current path, a deeper and narrower lesion 52 may be formed between monopolar electrode 40 and second electrode 46. As illustrated in FIG. 2, the present invention can provide a lesion formed entirely through the heart chamber wall, using an external electrode and the second, internal electrode.

Figures 3, 4, 5:
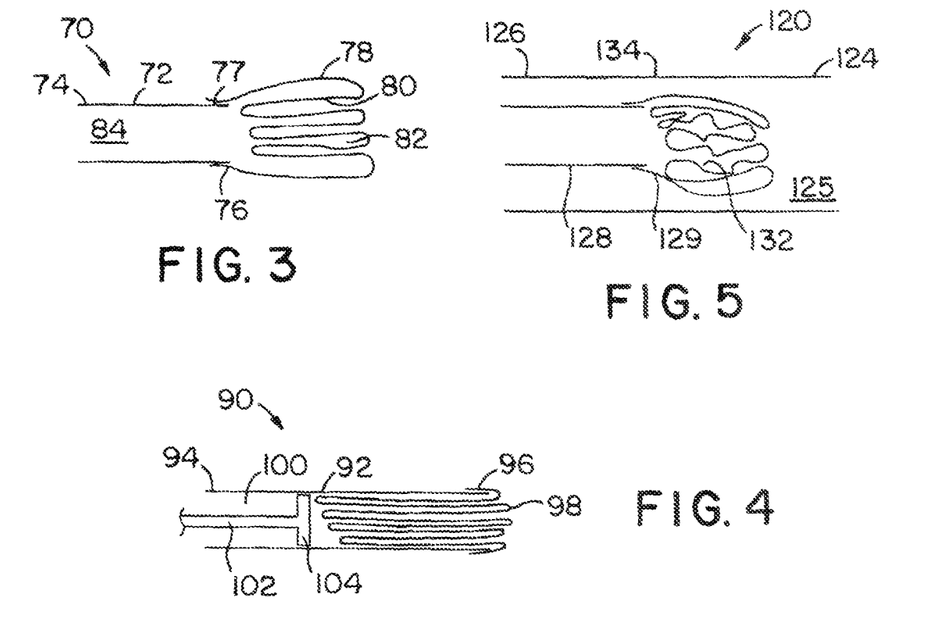
FIG. 3 is a diagrammatic, longitudinal cross-sectional view of one device having an expandable surface electrode, shown in an un-expanded configuration.
FIG. 4 is a diagrammatic, longitudinal cross-sectional view of another device having an expandable surface electrode, shown in an un-expanded configuration.
FIG. 5 is a diagrammatic, longitudinal cross-sectional view of yet another device having an expandable surface electrode, shown in an un-expanded configuration within a retractable delivery sheath.

FIG. 3 illustrates a device 70 that can be used to facilitate ablating cardiac tissue. Device 70 includes a device shaft 72 having an interior 84, a proximal region 74, and a distal region 76. An expandable envelope 78 may be seen affixed to shaft distal region 76. Envelope 78 is shown in a first, unexpanded configuration, having folds 80 and an internal volume, indicated at 82. Envelope 78 further includes a proximal mouth 77, secured to shaft distal region 77. As used herein, "expandable" refers to the envelope having an unexpanded and an expanded configuration, wherein the expanded configuration has a larger internal volume than the first configuration. The term "expandable" does not require that the envelope be elastic or stretchable in any way.

While some embodiments include a proximal shaft, other embodiments have no shaft. Some embodiments utilize the proximal mouth of the envelope or balloon to expand or inflate the envelope or balloon. In such embodiments, the balloon or envelope can be inserted into the heart chamber through an opening and inflated through a fluid supplied to the balloon proximal mouth.

Shaft 72 may be solid in some embodiments and hollow in other embodiments, carrying an inflation lumen within. In some embodiments, shaft 72 has a length of between about 12 and 18 inches. Some embodiments have a shaft length less than 12 inches, while other embodiments have a shaft length less than 6 inches. Some shafts have an outer diameter of between about 20 Fr. and 30 Fr. Shaft 72, and other shafts according to the present invention may be of shaft or tube materials well known to those skilled in the biomedical arts. Exemplary shaft materials include silicone, PEBAX, polyurethane, and PVC.

FIG. 4 illustrates another device 90 that can be used according to the present invention. Device 90 includes a shaft 92 having a proximal region 94 and a distal region 96. Shaft 92 further includes a lumen 100 within, carrying a proximal push rod 102 having a distal flange 104 attached to the push rod. An envelope 98 may be seen, in an unexpanded configuration within shaft lumen 100. In use, push rod 102 can be used to force envelope 98 out of shaft 92, allowing envelope 98 to expand. Envelope 98 may be self-expanding in some embodiments, and require fluid inflation, in other embodiments.

FIG. 5 illustrates still another device 120 having a shaft 128 having an envelope 132 secured to a shaft distal region 129. Envelope 132 may be seen to be in an unexpanded configuration. Envelope 132 may be seen to be in a compressed, folded state. Device 120 further includes an outer delivery sheath or sleeve 134 having a distal region 124 and a proximal region 126. Sleeve 134 can be proximally retracted from shaft 128 bearing envelope 132, or shaft 128 and envelope 132 can be distally urged out of delivery sleeve 134. In some embodiments, envelope 132 is self-expanding. In other embodiments, envelope 132 is inflated with fluid supplied through a lumen extending through shaft 128.

Figure 6:
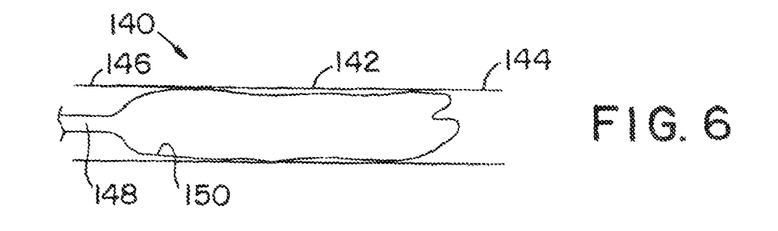
FIG. 6 is a diagrammatic, longitudinal cross-sectional view of still another device having an expandable surface electrode, shown in an un-expanded configuration within a retractable delivery sheath.

FIG. 6 illustrates still another device 140 having a delivery sheath 142 having distal region 144 and proximal region 146. An expandable envelope 150 may be seen, secured to a shaft 148. Shaft 148 and envelope 150 are both disposed within delivery sheath 142. In some embodiments, envelope 150 is biased to expand radially outward to form a spherical or bulbous shape, when unconstrained by outer sheath 142. In some embodiments, the envelope, for example, envelope 150, may be urged distally from a constraining tube, for example, sheath 142. After being distally urged from the outer tube, the envelope may be radially expanded and the outer tube used as a catheter to guide the now expanded envelope to the target site.

Figure 7:
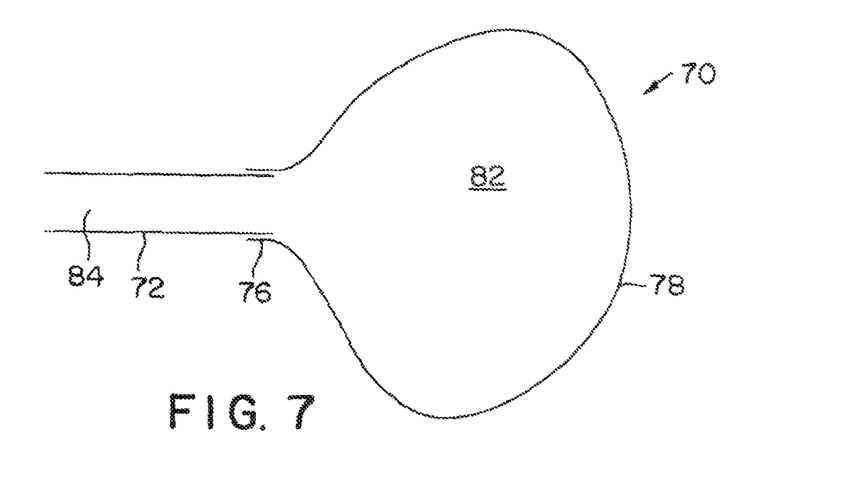
FIG. 7 is a diagrammatic, longitudinal cross-sectional view of a device having an expandable surface electrode, shown in an expanded configuration.

FIG. 7 illustrates device 70 of FIG. 3, in a second, expanded configuration. Device 70 may be seen to have a much larger envelope internal volume 82. Envelope 78 may be seen to be in a significantly expanded configuration relative to that seen in FIG. 3. In some embodiments, envelope 78 is self-expanding. In other embodiments, envelope 78 is inflated with fluid provided through a lumen provided through shaft 72, within shaft interior 84. In some methods, saline is used as the inflation fluid.

Figure 8:
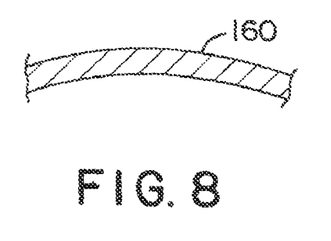
FIG. 8 is a fragmentary, cross-sectional view of an envelope formed of an electrically conductive material.

FIG. 8 illustrates a section of envelope material 160, wherein the entire thickness of the envelope material is electrically conductive. One such envelope material includes a conductive polymer.

Figure 9:
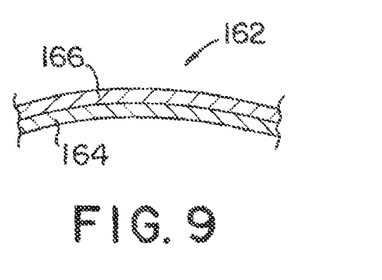
FIG. 9 is a fragmentary, cross-sectional view of an envelope formed of an electrically conductive material layer formed over another, more interior material.

FIG. 9 illustrates another envelope 162. Envelope 162 includes an inner layer 164 and an outer layer 166. In some embodiments, inner layer 164 is a polymeric, substantially nonconductive material. Outer layer 166 can be an electrically conductive material, for example, a metallic film. In some embodiments, envelope 162 is formed of Mylar, having a metallic film disposed over a polymeric layer.

Figure 10:
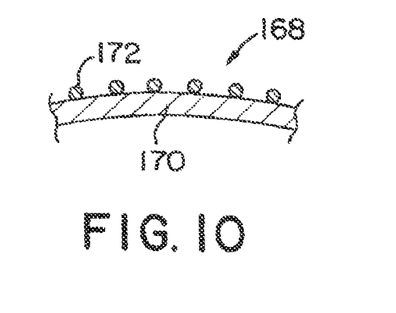
FIG. 10 is a fragmentary, cross-sectional view of an envelope formed of an electrically conductive mesh formed over another, more interior material.

FIG. 10 illustrates yet another envelope section 168 having an inner, substantially contiguous layer 170 and an outer mesh 172. In some embodiments, inner layer 170 is a polymeric layer that is substantially impervious to fluid flow, enabling the envelope to be fluid expanded. In some envelopes, mesh 172 is an electrically conductive, metallic mesh. Mesh 172 can be formed of Nitinol in some embodiments and stainless steel in other embodiments. In still other embodiments, electrically conductive mesh 172 is formed of an electrically conductive polymer. In some envelopes, mesh 172 is formed of a material biased to expand outwardly when unconstrained. In other embodiments, mesh 172 is formed of a shape memory material, set to expand outwardly when heated toward body temperature from room temperature. For the purposes of the present invention, room temperature may be defined as about 70 degrees Fahrenheit.

Figure 11:
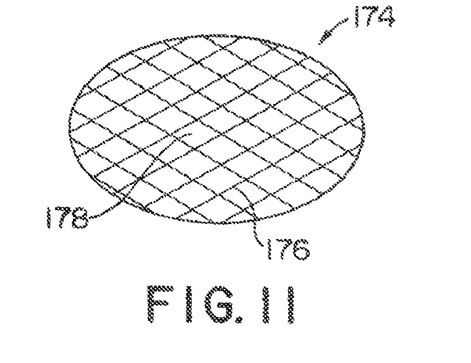
FIG. 11 is a fragmentary, side view of an envelope formed of an electrically conductive porous mesh.

FIG. 11 illustrates still another envelope section 174, having a porous mesh including braids or strands 176 having pores 178 disposed therebetween. In embodiments having a porous mesh, the mesh itself may be self-expandable or may be expanded through an inflation envelope disposed within the mesh.

In one method according to the present invention, a first RF electrode is provided, coupled to a RF current source. A second RF electrode is also provided and coupled to form a ground path for the first RF electrode. The second electrode can include an electrically conductive envelope surface defining an interior volume within. The envelope can have a first, unexpanded configuration and a second, expanded configuration. The second configuration can have an interior volume greater than the first, unexpanded configuration. An incision can be made in a heart chamber wall. A preferred use of the present invention is to ablate atrial wall tissue. One such incision is an incision made to remove an atrial appendage. Such incisions are typically made as part of a maze procedure.

After the incision is made, the second electrode can be inserted through the incision and into the heart chamber interior. The second electrode can then be expanded to urge the second electrode conductive surface to contact a target region of the heart chamber endocardium. The first electrode can be disposed against the target region epicardium while applying RF current through the first electrode.

A short, direct current path is thus formed between the first electrode on the epicardium and the expanded surface electrode bearing against the endocardium. The second electrode can be urged against tribiculated tissue to provide direct contact with the second electrode and therefore provide a short and direct current path directed through the tribiculated tissue. A lesion resulting from the current path formed between the first electrode and the second, interior electrode, can thus be both deeper and narrower than lesions formed using the external electrode and a remote indifferent electrode.

In some methods, the second electrode is biased to expand when unconstrained, and is freed from constraint after being inserted into the heart chamber through the incision. In some such methods, a sleeve or delivery tube is retracted from about the constrained second electrode. While some electrodes are simply biased to expand outward when unconstrained, other internal electrodes are formed of a shape memory material that expands when heated toward body temperature.

Some methods include providing a fluid expandable or inflatable envelope. In such methods, a fluid, for example, saline, can be injected into the envelope interior to expand the envelope to its fully expanded shape.

Applicant believes that the present invention provides novel methods for forming lesions entirely through the atrial wall using a first, external electrode on the epicardium and a second, expanded surface internal electrode on the endocardium, simultaneously. This may be contrasted with using an electrode drawn over the endocardial surface, for example, a pen electrode. While forming a lesion using an inserted pen electrode may be efficacious, a large incision must be made through the heart chamber wall in order to properly direct the drawing of the pen electrode across the endocardium. Using the present invention, an incision only large enough to insert the expandable or inflatable envelope need be made.

Applicant believes that target sites in the entire right and left atrial free wall regions may be ablated using RF ablation, and entirely through the atrial wall, where ablating these sites does not require making an incision in the right atrium from the excised atrial appendage parallel to the right atrioventricular groove toward the inferior vena cava (IVC), an incision from about 1 cm, above the IVC cannulation site to the top of the atrioventricular groove, or in the left atrium in the interatrial groove.

In general, the present invention provides methods for forming lesions in target tissue having a cavity within. In the general case of the invention, a first electrode is coupled to a RF current source and a second RF electrode is electrically coupled to form a ground path for the first RF electrode. The second electrode can be inserted into the tissue cavity and expanded to contact the target tissue from within the cavity. The first electrode can then be disposed against the target tissue from the outside, while applying RF current through the first electrode to ablate the target tissue.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. A method for forming a lesion in a target tissue having a cavity within, the method comprising:
   providing a first RF electrode coupled to one pole of an RF current source;
   providing a second RF electrode electrically coupled to the other pole of the RF current source, wherein the second RF electrode has an electrically conductive expandable surface defining an expandable interior volume;
   inserting the second electrode into the tissue cavity;
   expanding the interior volume of the second electrode such that the electrically conductive expandable surface contacts the target tissue from within the cavity; and
   disposing the first electrode against the target tissue while applying RF current between the first and second electrodes to ablate the target tissue.

2. A method as in claim 1, wherein the target tissue is atrial tissue and the cavity is the atria, wherein the expanding includes expanding the second electrode by inflating the electrode within the atria.

3. A method for performing a maze procedure to treat atrial fibrillation by ablating atrial tissue to form at least one lesion in the atrial tissue, the method comprising:
   providing a first RF electrode coupled to one pole of an RF current source;
   providing a second RF electrode electrically coupled to the other pole of the RF current source;
   inserting the second electrode into the atrial chamber; and
   disposing the first electrode against the target tissue and drawing paths with the first electrode to form the maze lesions while applying RF current between the first and second electrodes to ablate the target tissue in a maze pattern,
   wherein the inserting is done through an incision made to remove the right atrial appendage.

4. A method as in claim 3, wherein the method does not include making any other incisions in the right atrium.

5. A method as in claim 3, wherein the method does not include making an incision from the right atrial appendage incision toward the inferior vena caval orifice.

6. A method as in claim 3, wherein the method does not include making a posterior longitudinal incision starting caudal to the superior caval cannulation site at the dorsal aspect of the right atrium.

* * * * *